(12) United States Patent
Grimme et al.

(10) Patent No.: US 7,799,074 B2
(45) Date of Patent: Sep. 21, 2010

(54) ROTARY DISPLACEMENT PUMP WITH SMALLER RADIAL DIMENSIONS

(75) Inventors: Marc Grimme, Paris (FR); Jean-Marc Parquet, Domont (FR); Alain Carpentier, Paris (FR); Claude Wartelle, Gouvieux (FR)

(73) Assignee: Carmat, Paris (FR)

(*) Notice: Subject to any disclaimer, the term of this patent is extended or adjusted under 35 U.S.C. 154(b) by 89 days.

(21) Appl. No.: 12/294,585

(22) PCT Filed: May 7, 2007

(86) PCT No.: PCT/FR2007/000778
§ 371 (c)(1),
(2), (4) Date: Sep. 25, 2008

(87) PCT Pub. No.: WO2007/135261
PCT Pub. Date: Nov. 29, 2007

(65) Prior Publication Data
US 2009/0132038 A1 May 21, 2009

(30) Foreign Application Priority Data
May 12, 2006 (FR) .................................. 06 04206

(51) Int. Cl.
*A61M 1/10* (2006.01)
*F03C 2/00* (2006.01)
(52) U.S. Cl. ........................ 623/3.24; 623/3.1; 418/61.3
(58) Field of Classification Search ......... 623/3.1–3.26; 418/61.3
See application file for complete search history.

(56) References Cited

U.S. PATENT DOCUMENTS
2,458,958 A * 1/1949 Pigott et al. ................. 418/168

(Continued)

FOREIGN PATENT DOCUMENTS

| DE | 81 21 531 | 10/1985 |
|---|---|---|
| DE | 37 09 901 | 10/1988 |
| EP | 0 324 669 | 7/1989 |
| EP | 0 560 709 | 9/1993 |
| FR | 1 504 705 | 10/1967 |
| FR | 2 760 973 | 9/1998 |

OTHER PUBLICATIONS

International Search Report dated Sep. 13, 2007 w/ English translation.
Written Opinion of the International Searching Authority with English translation.

*Primary Examiner*—Suzette J Gherbi
(74) *Attorney, Agent, or Firm*—Dickinson Wright PLLC

(57) ABSTRACT

According to the invention the rotary pump consists of an external gear (13) with internal teeth (16) in the form of a squirrel cage, and an internal gear (9), housed in an off-centre manner in the interior of said external gear (13) and fitted with external teeth (9D) intermeshing with said internal teeth (16) and consisting of a number of inferior teeth of a unit with the number of teeth of the later. The rotation means of said external teeth (13) comprise at least a bearing (11, 12) centrally laid out in a flange end (14,15) of said aforementioned external gear (13) and the aforementioned external gear (13) is at least partly dismantled in order to introduce said internal gear (9).

9 Claims, 6 Drawing Sheets

U.S. PATENT DOCUMENTS

| | | | |
|---|---|---|---|
| 3,386,648 A * | 6/1968 | Van Rossem | 418/108 |
| 5,135,539 A | 8/1992 | Carpentier | |
| 5,373,819 A * | 12/1994 | Linder | 123/238 |
| 6,342,072 B1 | 1/2002 | Wartelle | |
| 6,979,351 B2 * | 12/2005 | Forsell et al. | 623/3.1 |

* cited by examiner

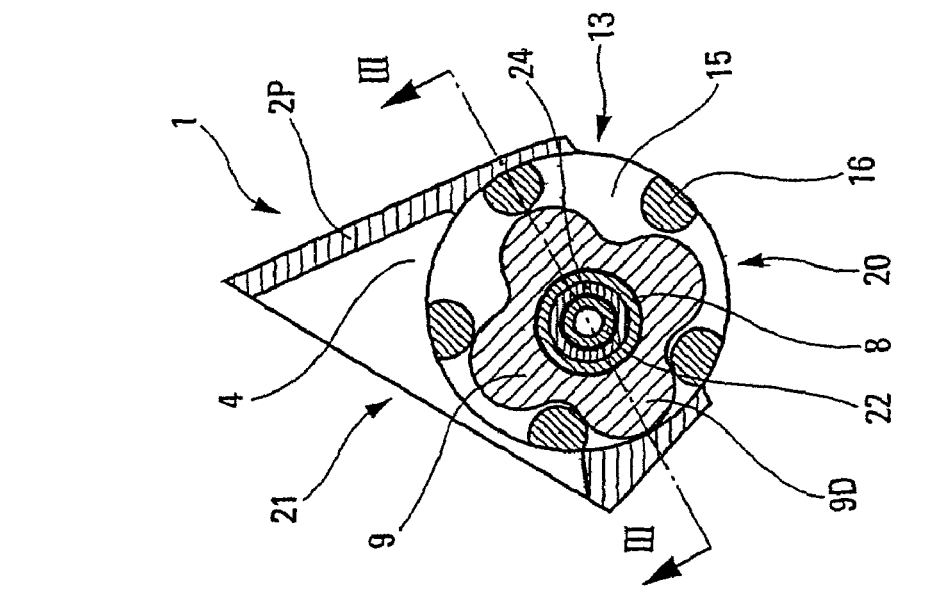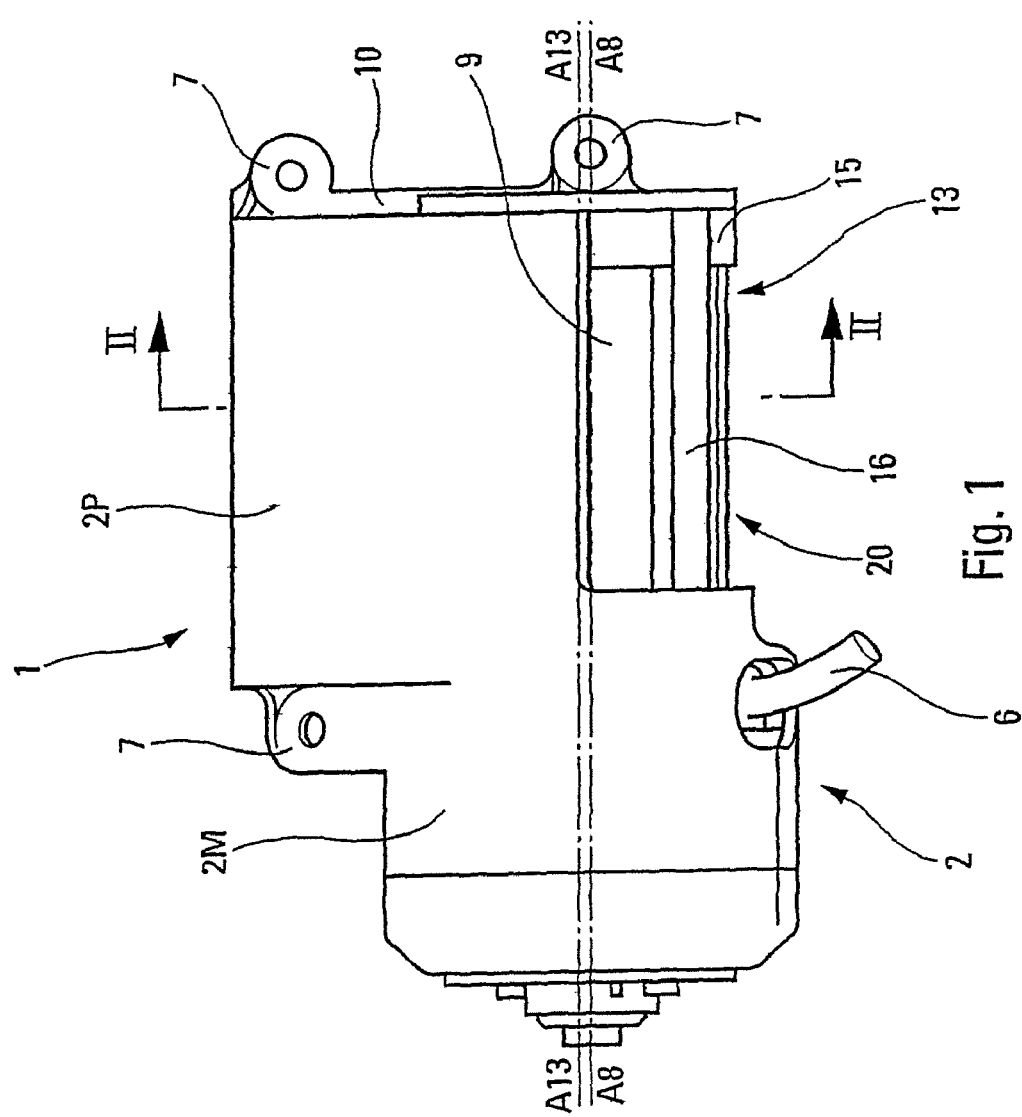

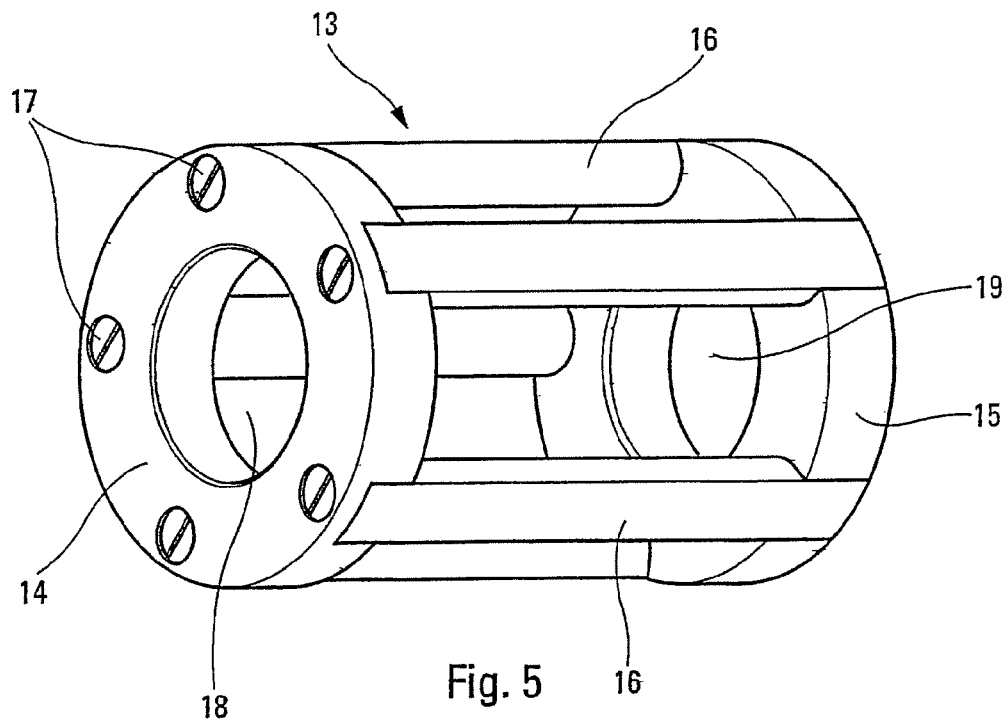
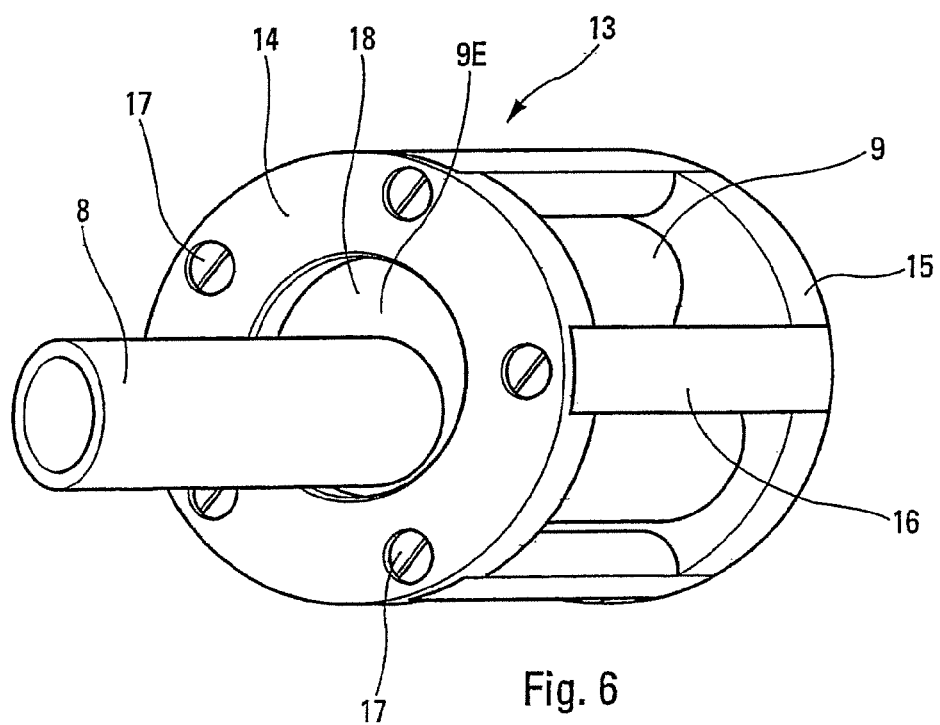

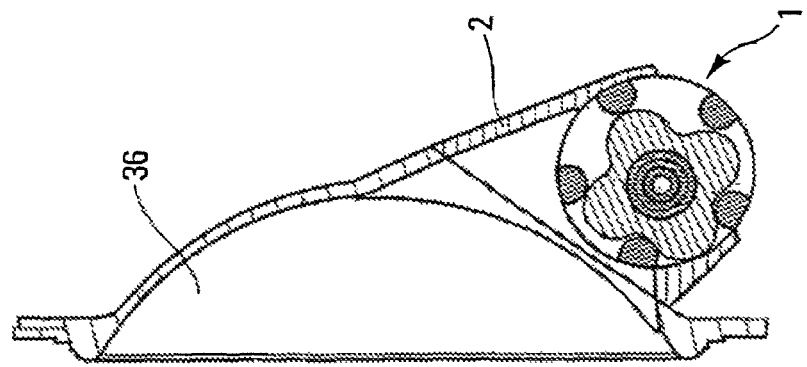
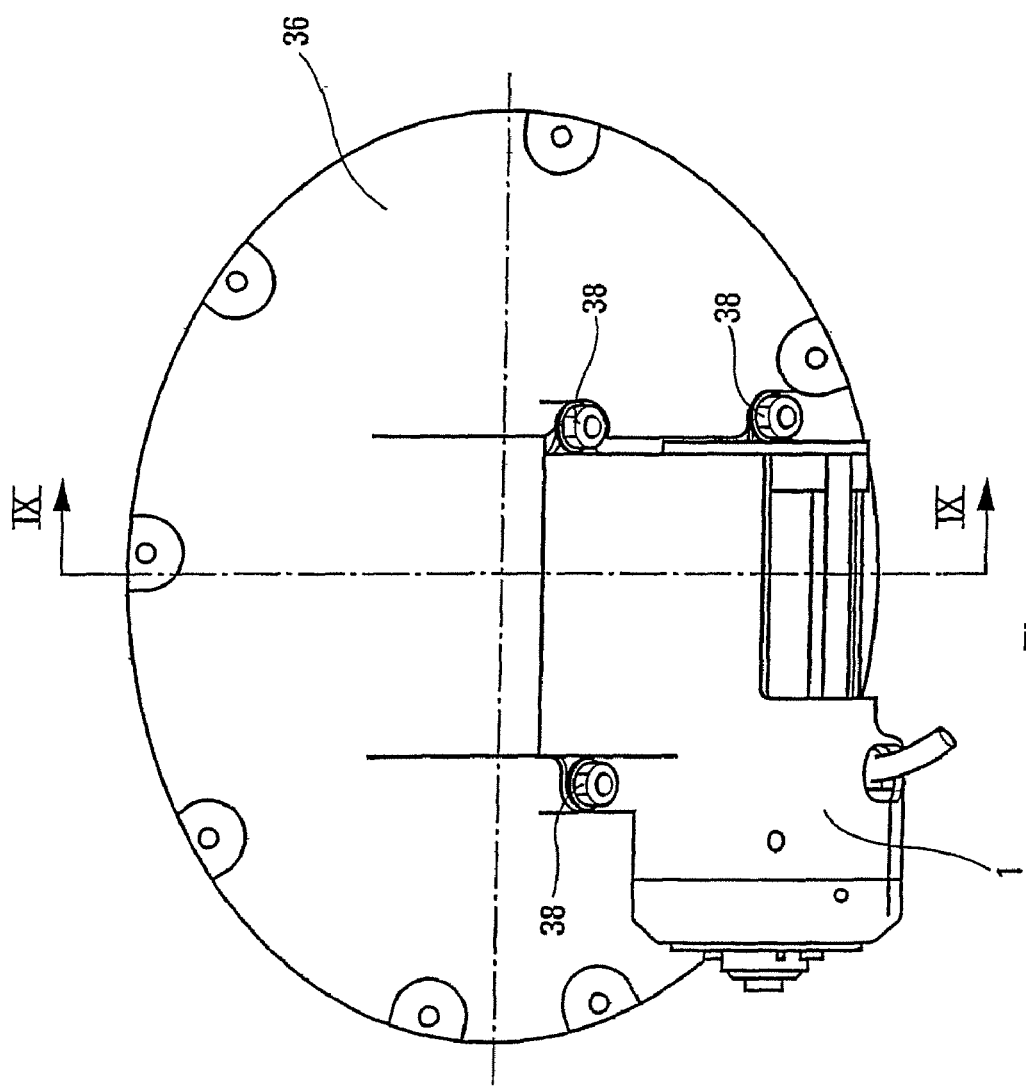
Fig. 9
Fig. 8

ROTARY DISPLACEMENT PUMP WITH SMALLER RADIAL DIMENSIONS

The present invention relates to a rotary displacement pump with smaller radial dimensions.

Documents U.S. Pat. No. 2,458,958, FR-1 504 705, EP-0 560 709 and DE-81 21 531 U1 already disclose a rotary displacement pump comprising:

a casing in which there are a pumping chamber and a radial fluid inlet and outlet for said pumping chamber;

an outer gear with an internal toothset positioned inside said pumping chamber and displaying the shape of a squirrel cage provided with two end plates which are connected by longitudinal bars that form said internal toothset, said outer gear being at least partially dismantleable;

rotation means allowing said outer gear to rotate inside said pumping chamber about a first axis and comprising at least one bearing positioned centrally in an end plate of said outer gear;

an inner gear, housed inside said outer gear and provided with an external toothset meshing with said internal toothset of the outer gear, said inner gear rotating about a second axis, parallel to and distant from said first axis, and said external toothset comprising a number of teeth lower by one unit than the number of teeth of the internal toothset of said outer gear; and a motor for driving the rotation of said inner gear about said second axis.

It is an object of the present invention to improve a rotary displacement pump of this type in order to reduce the radial dimensions thereof while at the same time allowing said inner gear to be fitted into and removed from said outer gear.

To these ends, according to the invention, the rotary displacement pump of the type described hereinabove is noteworthy in that:

said pumping chamber comprises a removable wall capable of being fixed to said casing to close off said pumping chamber, and a bearing of said rotation means is positioned in said removable wall;

a bearing of said rotation means is positioned in a fixed wall of said pumping chamber;

said casing comprises a housing for said motor and said fixed wall separates said housing from said pumping chamber;

the shaft of the motor driving the rotation of the inner gear passes through said fixed wall inside said bearing; and said shaft of the motor is hollow and through it there passes, with clearance, a tie rod used to fix said removable wall to said casing.

As a preference, at least one of the end plates of said outer gear is dismantleable.

Furthermore, it is advantageous for bearings for said motor shaft, that is to say for said inner gear, to be positioned on said tie rod.

When the pump according to the present invention is, intended to be immersed in a hydraulic liquid, said tie rod may itself be hollow so that said liquid can enter it, and the side wall of said tie rod may be pierced with orifices. In this way, said bearings of the inner gear, carried by said tie rod, can be lubricated with said hydraulic liquid.

In order to avoid the risks of cavitation and turbulent losses in the fluid displaced by the pump, it is advantageous for said radial fluid inlet and/or for said radial fluid outlet to extend from one end plate of said outer gear to the other.

For the same reasons, the internal toothset of the outer gear and the internal toothset of the outer gear comprise five at the most, and four teeth, respectively. Thus, the outside diameter of said pump can be smaller, this accordingly reducing the velocities of the fluid around the periphery of said pump.

Thanks to the specific features described hereinabove it will be readily understood that the pump according to the present invention can be miniaturized, while at the same time having a reversible output.

According to one example of an application thereof, the miniaturized pump according to the present invention can be incorporated into a heart prosthesis that can be implanted in the pericardial cavity of a patient.

Thus, a heart prosthesis such as this, which can replace the native left and right ventricles of said patient once these have been removed and which comprises a body in which artificial left and right ventricles operated by at least one hydraulic actuator are arranged, is notable in that said hydraulic actuator is a displacement pump like the one specified hereinabove.

If, as is customary, the artificial ventricles have a cover plate attached to said prosthesis body, it is then advantageous, according to the invention, for a displacement pump such as this to be connected to such a cover plate.

The figures of the attached drawing will make it easy to understand how the invention may be embodied. In these figures, identical references denote elements that are similar.

FIG. 1 is a view from above of one small-sized embodiment of the rotary displacement pump according to the present invention.

FIG. 2 is a cross section on II-II of FIG. 1.

FIG. 5 is a perspective view of the outer gear.

FIG. 6 is a perspective view of the outer gear and inner gear assembly.

FIG. 8 is a view from above of the pump of FIGS. 1 to 3, mounted on a ventricle cover plate.

FIG. 9 is a cross section on IX-IX of FIG. 8.

Figure 3:
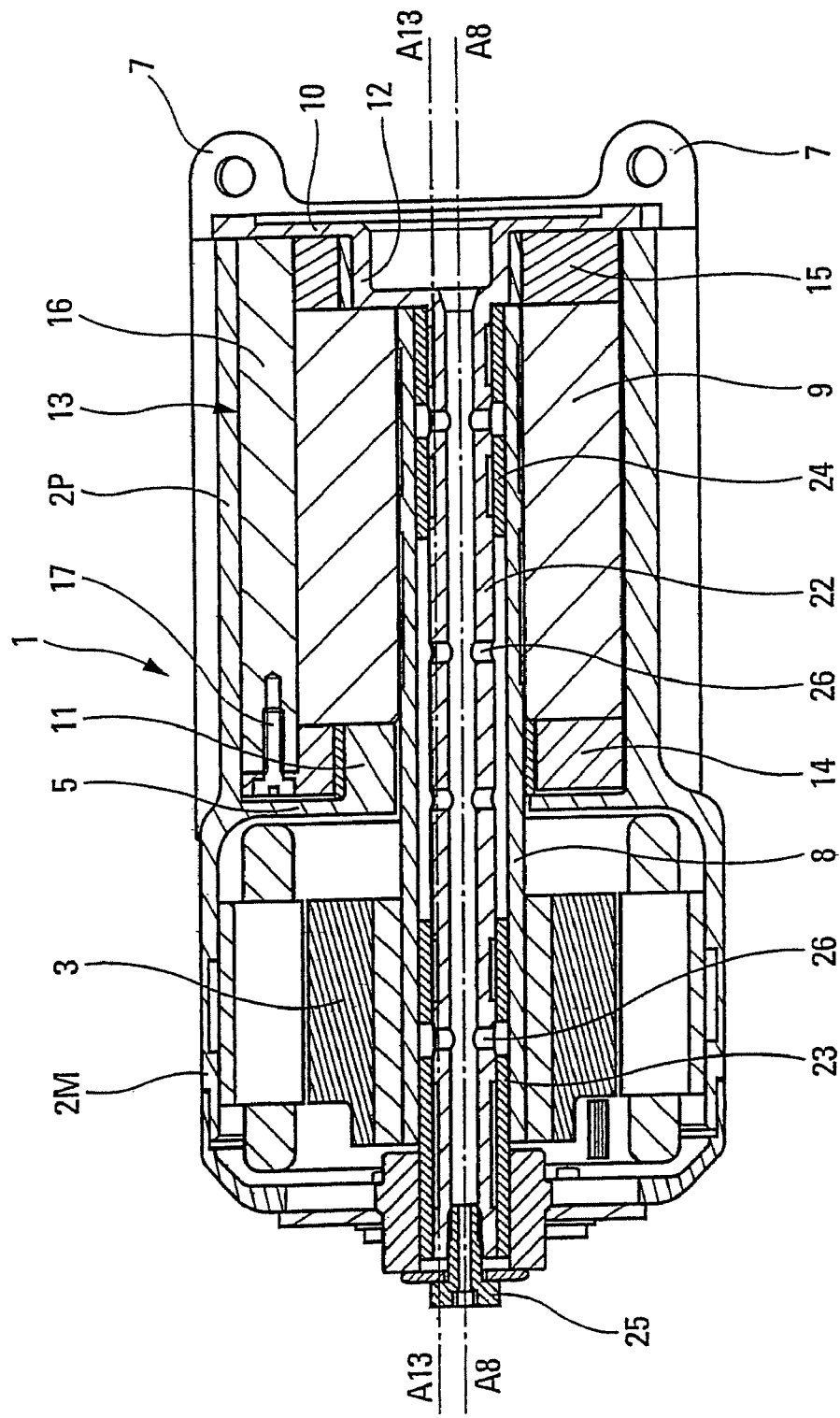
FIG. 3 is an axial section on III-III of FIG. 2.
Figure 4:
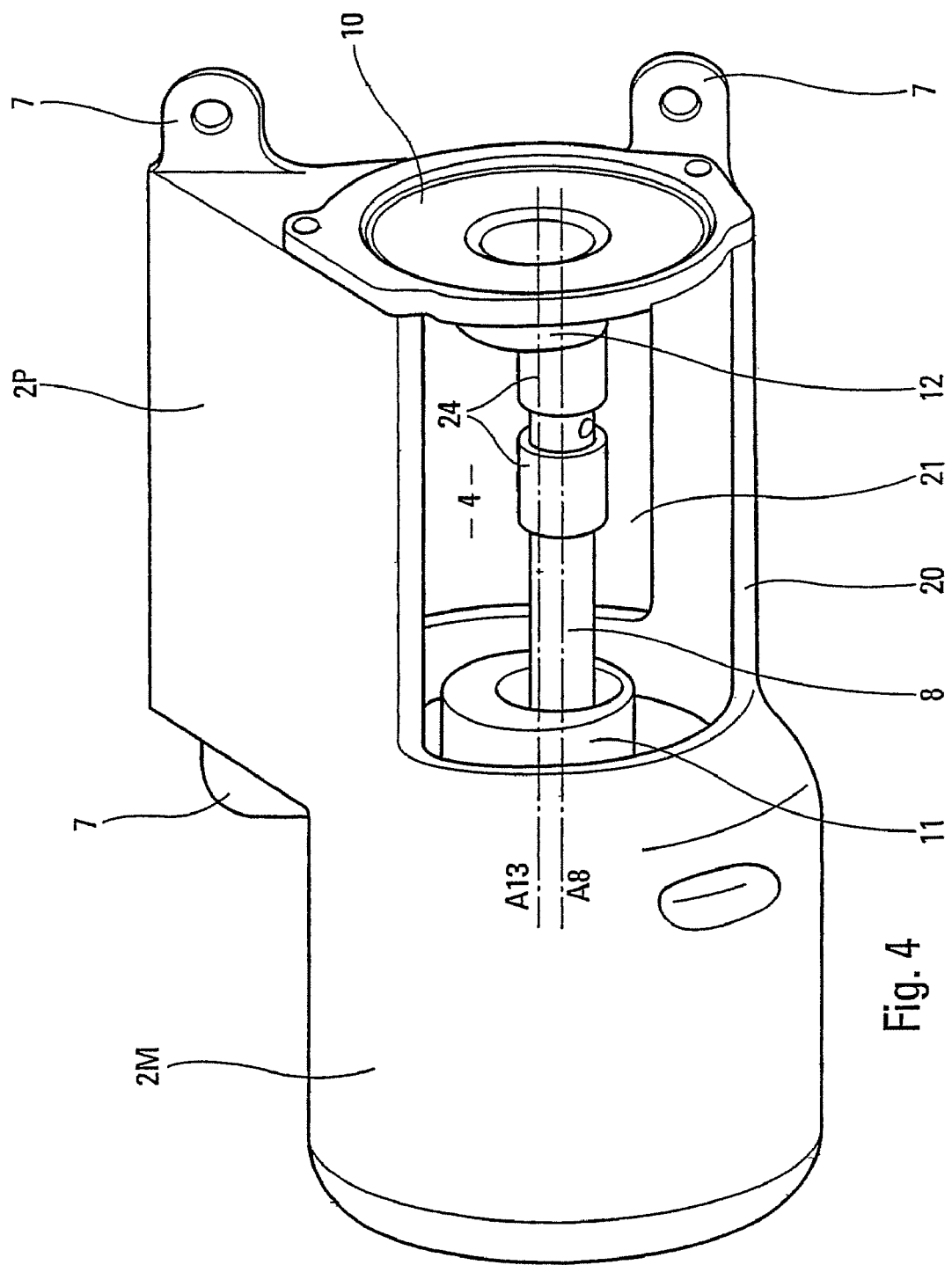
FIG. 4 is a perspective view of the pump of FIGS. 1 to 3, from which the outer and inner gears have been removed.

The rotary displacement pump 1 according to the present invention and illustrated by FIGS. 1 to 6 comprises a casing 2 comprising a part 2M in which an electric motor 3 is housed, and a part 2P in which a pumping chamber 4 is arranged. The parts 2M and 2P of the casing 2 are separated from one another by a fixed internal wall 5 that forms an integral part of said casing 2. The electric motor 3 is powered by an electric lead 6 passing through the casing part 2M and said casing 2 is provided with fixing lugs 7.

The rotary shaft 8 of the electric motor 3 has an axis A8 and passes through the fixed internal wall 5 to enter the pumping chamber 4. Keyed onto that part of said shaft 8 that is housed in the pumping chamber 4 is an elongate gear 9 with four rounded external teeth 9D.

The part 2P of the casing 2, that forms said pumping chamber 4, is open at its opposite end to the part 2M and which can be closed off in a fluidtight manner by a removable wall 10 that can be fixed to said casing 2.

Arranged in said fixed internal wall 5 and in said removable wall 10, respectively, on the same side of said pumping chamber 4 and facing one another, are bearings 11 and 12 defining an axis A13 for a gear 13 housed in said pumping chamber 4.

The axis A13 is parallel to the axis A8 but offset therefrom.

The gear 13 displays the form of a squirrel cage provided with two end plates 14 and 15 which are connected by five longitudinal bars 16 that form rounded internal teeth for said gear 13. In the example depicted in the figures, the bars 16 are secured to the end plate 15 while the end plate 14 is removable, being attached by way of screws 17, allowing it to be separated from the end plate 15 and from the bars 16.

The end plates 14 and 15 are respectively provided with central circular recesses 18 and 19 capable respectively of collaborating with the bearings 11 and 12 to allow said gear 13 to rotate inside said pumping chamber 4.

The gear 9 is housed inside the gear 13, with its end faces 9E respectively in the vicinity of the end plates 14 and 15 and the shaft 8 passing through the central circular recess 18 of the end plate 14. It will be readily understood that, thanks to the fact that the end plate 14 can be removed, it is easy to fit the gear 9 inside the gear 13.

When the gear 13 is mounted on the bearings 11 and 12 and the gear 9 is positioned inside said gear 13 and keyed onto the shaft 8, the respective rounded teeth 9D and 16 of said gears are capable of collaborating with one another in order to produce a pumping effect.

Furthermore, that part 2P of the casing 2 that defines the pumping chamber 4 has two opposing openings 20 and 21 extending over the length of the gear 9 and capable respectively of acting as radial inlet and outlet for the fluid that is to be pumped.

Thus, when the motor 3, via the shaft 8, drives the rotation of the gear 9 about the axis A8, the rounded external teeth 9D of said gear 9 collaborate with the rounded internal teeth 16 of the gear 13 to drive the latter gear in rotation about the axis A13 of the bearings 11 and 12. As it does so, fluid is drawn in through the inlet 20 and discharged through the outlet 21.

As can be seen clearly in FIG. 3, the shaft 8 of the motor 3 and of the inner gear 9 is hollow and a tie rod 22, secured to the removable wall 10, passes through it with clearance. Bearings 23, 24 are carried by the tie rod 22 and participate in the rotating of the inner gear 9. A screw 25, engaged on the free end of said tie rod 22, bears against the end of the casing 2, the opposite end to the removable wall 10, in order to press said removable wall 10 firmly against said casing.

The screw 25 and the tie rod 22 are hollow and apertures 26 are pierced in the side wall of the tie rod 22.

Thus, when the pump 1 is immersed in hydraulic liquid, this liquid can lubricate said bearings 23, 24 of the inner gear 9.

Figure 7:
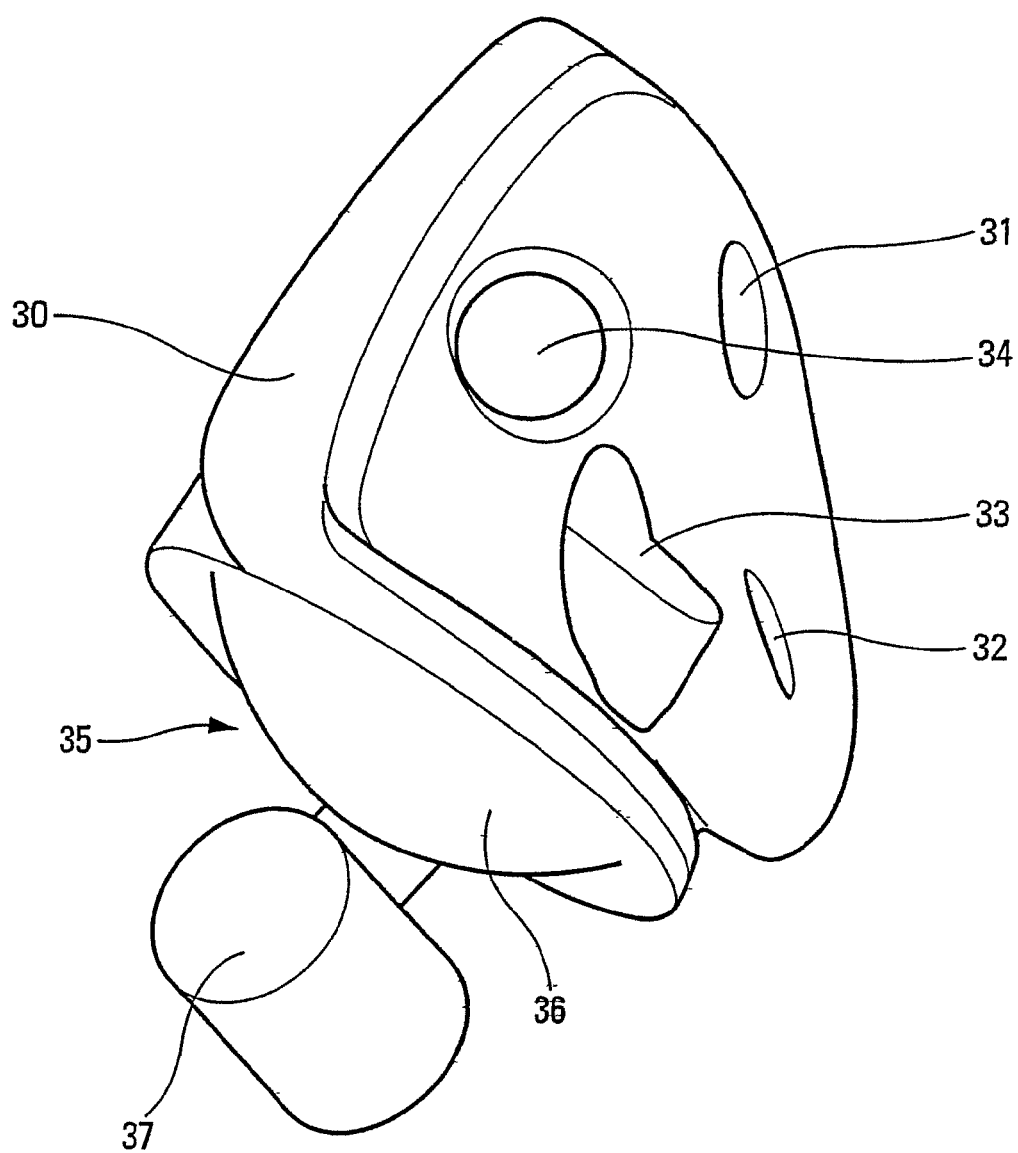
FIG. 7 is a perspective view, shown schematically and partially, of a heart prosthesis equipped with a hydraulic actuator.

FIG. 7 schematically depicts a perspective view of the body 30 of a heart prosthesis that can be implanted after the native ventricles of a patient have been removed and which is provided with apertures 31 to 34 for connecting, respectively, to the right atrium, to the left atrium, to the aorta and to the pulmonary artery of said patient. This FIG. 7 indicates, on the outside of said body 30, the site of an artificial ventricle 35, closed off by a cover plate 36 bearing an actuator 37 for said ventricle.

FIGS. 8 and 9 show one embodiment of the cover plate 36 for the artificial ventricle 35, in which said actuator 37 is formed by the pump 1 according to the present invention, said pump 1 being fixed to said cover plate 36 by bolts 38 passing through the lugs 7.

The invention claimed is:

1. A rotary displacement pump comprising:
   a casing (2) in which there are a pumping chamber (4) and a radial fluid inlet (20) and outlet (21) for said pumping chamber (4);
   an outer gear (13) with an internal toothset (16) positioned inside said pumping chamber (4) and displaying the shape of a squirrel cage provided with two end plates (14, 15) which are connected by longitudinal bars that form said internal toothset, said outer gear (13) being at least partially dismantleable;
   rotation means (11, 12) allowing said outer gear (13) to rotate inside said pumping chamber (4) about a first axis (A13) and comprising at least one bearing (11, 12) positioned centrally in an end plate (14, 15) of said outer gear (13);
   an inner gear (9), housed inside said outer gear (13) and provided with an external toothset (9D) meshing with said internal toothset (16) of the outer gear (13), said inner gear (9) rotating about a second axis (A8), parallel to and distant from said first axis (A13), and said external toothset (9D) comprising a number of teeth lower by one unit than the number of teeth of the internal toothset of said outer gear (13); and
   a motor (3) for driving the rotation of said inner gear (9) about said second axis (A8), wherein:
   said pumping chamber (4) comprises a removable wall (10) capable of being fixed to said casing (2) to close off said pumping chamber (4), and a bearing (12) of said rotation means is positioned in said removable wall (10);
   a bearing (11) of said rotation means is positioned in a fixed wall (5) of said pumping chamber (4);
   said casing (2) comprises a housing (2M) for said motor (3) and said fixed wall (5) separates said housing (2M) from said pumping chamber (4);
   the shaft (8) of the motor (3) driving the rotation of the inner gear (9) passes through said fixed wall (5) inside said bearing (11); and
   said shaft (8) of the motor (3) is hollow and through it there passes, with clearance, a tie rod (22) used to fix said removable wall (10) to said casing (2).

2. The displacement pump as claimed in claim 1, wherein at least one of the end plates (14, 15) of said outer gear (13) is dismantleable.

3. The displacement pump as claimed in claim 1, wherein bearings (23, 24) for said inner gear (9) are positioned on said tie rod (22).

4. The displacement pump as claimed in claim 3, intended to be immersed in a hydraulic liquid, wherein said tie rod (22) is hollow so that said liquid can enter it, and the side wall of said tie rod (22) is pierced with orifices (26).

5. The displacement pump as claimed in claim 1, wherein said radial fluid inlet (20) extends from one end plate of said outer gear (13) to the other.

6. The displacement pump as claimed in claim 1, wherein said radial fluid outlet (21) extends from one end plate of said outer gear (13) to the other.

7. The displacement pump as claimed in claim 1, wherein the internal toothset (16) of the outer gear (13) comprises five teeth at the most, whereas the external toothset of the inner gear (9) has, at most, fourth teeth (9D).

8. A heart prosthesis that can be implanted in the pericardial cavity of a patient, said prosthesis being capable of replacing the native left and right ventricles of said patient once these have been removed and comprising a body (30) in which artificial left and right ventricles (35) operated by at least one hydraulic actuator (37) are arranged, wherein said hydraulic actuator is a displacement pump (1) like the one specified in claim 1.

9. The heart prosthesis as claimed in claim 8, in which the artificial ventricles (35) comprise a cover plate (36) attached to said body (30), wherein the displacement pump is connected to such a cover plate (36).

* * * * *